United States Patent [19]

Lang

[11] Patent Number: 5,801,245
[45] Date of Patent: Sep. 1, 1998

[54] PROCESS FOR THE PREPARATION OF ETHYL-N-(2,3 DICHLORO-6-NITROBENZYL) GLYCINE

[75] Inventor: Philip C. Lang, Toms River, N.J.

[73] Assignee: Roberts Laboratories Inc., Eatontown, N.J.

[21] Appl. No.: 919,964

[22] Filed: Aug. 28, 1997

Related U.S. Application Data

[63] Continuation of Ser. No. 566,862, Dec. 4, 1995, abandoned.

[51] Int. Cl.$^6$ ............................................. C07D 239/00
[52] U.S. Cl. ................................... 544/250; 544/249
[58] Field of Search .......................... 540/522; 544/250

[56] References Cited

U.S. PATENT DOCUMENTS

| Re. 31,617 | 6/1984 | Beverung et al. | 544/250 |
|---|---|---|---|
| 1,947,926 | 2/1934 | Steindorff et al. | 167/38 |
| 2,256,999 | 9/1941 | Castner | 260/645 |
| 2,469,695 | 5/1949 | McNally | 260/490 |
| 2,608,584 | 8/1952 | Sprules et al. | 260/570.9 |
| 2,732,403 | 1/1956 | Surrey | 260/562 |
| 2,862,966 | 12/1958 | Surrey | 260/562 |
| 2,883,435 | 4/1959 | Welch | 260/646 |
| 3,313,854 | 4/1967 | Levy | 260/576 |
| 3,928,476 | 12/1975 | Shimada et al. | 260/646 |
| 3,932,407 | 1/1976 | Beverung, Jr. et al. | 260/256.4 |
| 4,036,838 | 7/1977 | Vogel et al. | 260/251 |
| 4,146,718 | 3/1979 | Jenks et al. | 544/292 |
| 4,208,521 | 6/1980 | Crenshaw et al. | 544/250 |
| 4,357,330 | 11/1982 | Fleming, Jr. et al. | 424/232 |

FOREIGN PATENT DOCUMENTS

| 278754 | 2/1970 | Austria. |
|---|---|---|
| 0 546 697 A1 | 6/1992 | European Pat. Off.. |
| 17-17893 | 9/1942 | Japan. |
| 47-19261 | 6/1972 | Japan. |

OTHER PUBLICATIONS

CA 112:216689 Kudo, 1989 Oct. 16 Preparation of Pthalimide Derivatives.
Organic Chemistry, Morrison & Boyd 3rd Edition 1975 344–347.
Aldrich Catalogue 1996, p. 498.
Morrison & Boyd "Organic Chemistry" 3rd Edition 1975 pp. 387–388.

*Primary Examiner*—Gary Geist
*Assistant Examiner*—Jean F. Vollano
*Attorney, Agent, or Firm*—DeLio & Peterson, LLC

[57] ABSTRACT

The known blood platelet reducing agent Anagrelide is prepared via an improved process starting with commercially available 2,3-dichlorotoluene and involving novel intermediates represented by the formulas:

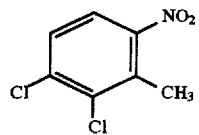

(F)

and

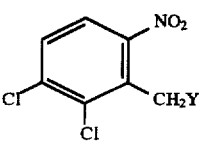

(G)

wherein Y is Br, Cl or I. Compound (G) is reacted with ethyl glycine to form the well-known intermediate ethyl-N-(2,3-dichloro-6-nitro benzyl) glycine which is then used following conventional process steps to form Anagrelide.

4 Claims, No Drawings

PROCESS FOR THE PREPARATION OF ETHYL-N-(2,3 DICHLORO-6-NITROBENZYL) GLYCINE

This is a continuation of application Ser. No. 08/566,862 filed on Dec. 4, 1995, now abandoned.

BACKGROUND OF THE INVENTION

1. Field of the Invention

This invention relates to a new and improved process for the preparation of the known platelet reducing compound 6,7-dichloro-1,5 dihydroimidazo [2,1-b]quinazolin-2(3H)-one via alkyl-N-(2,3-dichloro-6-nitrobenzyl) glycine and salts thereof which known glycine intermediate compound is prepared via novel intermediates 2,3-dichloro-6-nitrotoluene and 2,3-dichloro-6-nitrobenzylhalide.

2. Description of Related Art

U.S. Pat. No. 3,932,407 and its Reissue Pat. No. Re. 31,617, which patents are hereby incorporated by reference, disclose compounds of the formula:

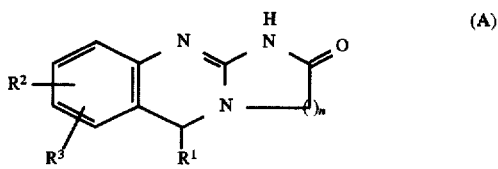

in which $R^1$ is H, phenyl or lower alkyl, $R^2$ and $R^3$ when alike are H, chloro, bromo, fluoro, lower alkyl, hydroxy or lower alkoxy, $R^2$ and $R^3$ when different are H, chloro, bromo, fluoro, $SO_3H$, $CF_3$, hydroxy, nitro, amino, phenyl, lower alkyl of 1 to 3 carbon atoms or lower alkoxy of 1 to 3 carbon atoms, or when taken together $R^2$ and $R^3$ are methylenedioxy or the residue of a phenyl ring, and n is an integer of 1 or 2; and pharmaceutically acceptable acid addition salts thereof. The compounds, which are disclosed as hypotensive, blood platelet reducer and/or bronchodilator agents, are prepared inter alia by a multistep process ending in the reaction of CNBr with an ethanol solution of a compound of the formula:

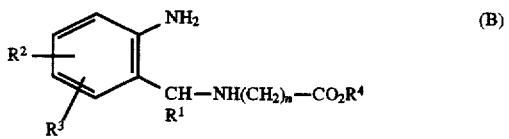

in which $R^1$, $R^2$, $R^3$ and n are as described above, and $R^4$ is lower alkyl.

Anagrelide having the chemical name 6,7-dichloro-1,5-dihydroimidazo[2,1-b]quinazolin-2[3H]-one and the structural formula:

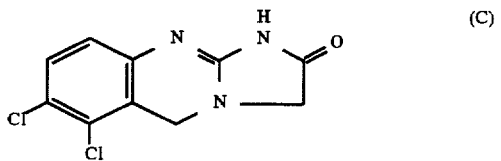

is of particular interest because it is known to be a potent reducer of platelet count induced by a variety of aggregating agents.

Anagrelide may be prepared directly from a lower alkyl-N-(6-amino-2,3-dichlorobenzyl)glycine of Formula (B) by reaction in an alcoholic solution with CNBr. U.S. Pat. No. 4,146,718 incorporated herein by reference discloses an improved process whereby higher yields of Anagrelide may be obtained by reacting a compound of Formula (B) with, for example, CNBr, CNCl or CNI in an inert, aprotic organic solvent and isolating the novel intermediate of Formula D.

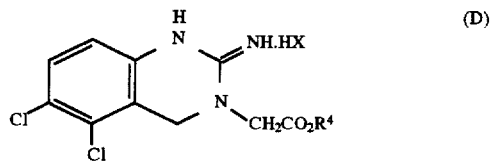

wherein $R^4$ is (lower)alkyl and X is chloro, bromo or iodo. In a preferred embodiment X is bromo and $R^4$ is methyl, ethyl, n-propyl, isopropyl or n-butyl. In a more preferred embodiment X is bromo and $R^4$ is methyl, ethyl or n-propyl. In a most preferred embodiment X is bromo and $R^4$ is ethyl.

Intermediate Compound (D) is then treated with a base to produce the compound of Formula A which includes the preferred Compound (C) Anagrelide. The yield of Compound A obtained in this two-step procedure typically is about four times greater than the yield obtained in the one-step process.

Regardless of the process used however, Compound (B) is an important intermediate in the Anagrelide process and Compound (B) is conventionally prepared by reacting $SnCl_2$ and HCl with alkyl-N-(2,3-dichlor-6-nitrobenzyl) glycine of the formula:

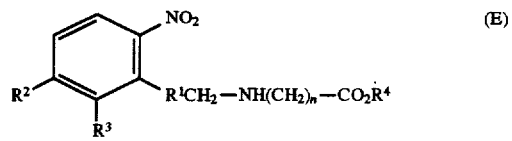

in which $R^1$, $R^2$, $R^3$, $R^4$ and n are defined as above and for the preferred Compound (B) $R^2$ and $R^3$ are both Cl, $R^1$ is H and $R^4$ is $C_2H_5$.

Commercially, Compound (E) has been conventionally prepared from (2,3-dichloro-6-nitrobenzylamine) but this material is no longer commercially available because of the toxic and extreme skin irritation properties of its precursor (2,3-dichloro-nitrobenzonitrile). The conventional synthesis route to make Compound (B) and its precursor Compound (E) from 1,2,3-trichlorobenzene is shown in U.S. Pat. No. 4,146,718.

Bearing in mind the problems and deficiencies of the prior art it is an object of the present invention to provide a synthesis route to prepare Compound (B) and its precursor Compound (E) using commercially available starting materials and reactants and which synthesis route is environmentally acceptable.

Another object of the invention is to provide a novel synthesis process and intermediate compound of the formula:

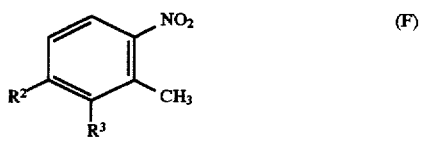

A further object of the invention is to provide a novel synthesis process and intermediate compound of the formula:

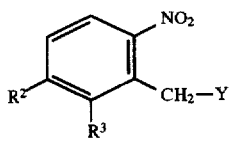

wherein for both Compounds (F) and (G), $R^2$ and $R^3$ are defined as above and Y is preferably Br, Cl or I.

It is still a further object of the invention to provide a synthesis route to make compounds of Formula A such as the preferred Anagrelide starting with commercially available reactants such as 1,2-dichlorotoluene.

Still other objects and advantages of the invention will in part be obvious and will in part be apparent from the specification.

SUMMARY OF THE INVENTION

The above and other objects and advantages, which will be apparent to those skilled in the art, are achieved in the present invention which is directed to a process for making precursor Compound (E), used in the preparation of Anagrelide and other compounds of formula (A), and having the formula:

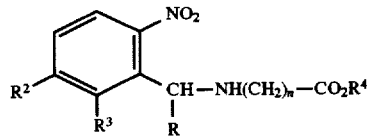

wherein $R^2$ and $R^3$ are each independently selected from the group consisting of H, Br, Cl and I, $R^4$ is lower alkyl, e.g., $C_1$–$C_5$ alkyl or H and $R^1$ is H or lower alkyl, e.g., $CH_3$, and n is an integer of 1 or 2 which process comprises:

(a) nitrating a compound of the formula:

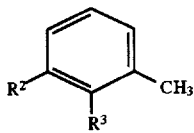

to form a compound of the formula:

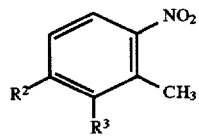

(b) reacting Compound (F) under free radical conditions to form a compound of the formula:

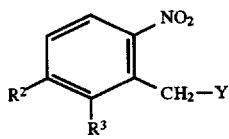

wherein Y is preferably Br, Cl or I; and (c) reacting Compound (G) with a compound of the formula:

to form Compound (E).

DESCRIPTION OF THE PREFERRED EMBODIMENTS

As used herein, the term lower alkyl means a straight or branched chain alkyl group containing from about 1 to 6 carbon atoms. The term "free radical conditions" used to describe halogenation of an alkyl group such as the $CH_3$ attached to an aromatic ring, is generally known in the art to be performed using ultra violet light and/or benzoyl peroxide, and/or peroxy acids such as peracetic acid to initiate the reaction. Reactants generally include $SO_2Cl_2$, $SO_2Br_2$, $Cl_2$, $Br_2$, $I_2$ and N-bromo succinimide. Exemplary inert aprotic organic solvents includes carbon tetrachloride, benzene, chlorobenzene and cyclohexane.

EXAMPLE 1

Preparation of 2,3-dichloro-6-nitrotoluene 208 mmole concentrated nitric acid and 270 mmole concentrated sulfuric acid were mixed and cooled to ambient temperature. 200 mmole 2,3-dichlorotoluene was added to a reaction flask and was cooled in an ice-water bath. The acid mixture was added slowly with stirring to the dichlorotoluene keeping the dichlorotoluene in the ice-water bath. After all the acid had been added, the mixture in the ice-water bath was stirred for about 10 minutes. A drying tube was attached to the reaction flask and the reaction mixture warmed to ambient temperature. The reaction mixture was heated at 50° C. with stirring for three hours.

The reaction mixture was transferred to a separatory funnel and the acid drained. The organic layer was washed with water and discarded. 1 % sodium carbonate was added to neutralize the acid. Ethyl acetate was added and partitioned the product to the organic phase. Ethyl acetate was added until the organic phase cleared. The organic phase was washed with water, followed by washing with half-saturated aqueous brine solution and washing with saturated aqueous brine solution. The organic phase was dried with sodium sulfate and the solvent evaporated under reduced pressure.

The crude product was purified by flash column chromatography using silica gel 60 (35 to 70-um particle size) at 5% product loading. The elution solvent was 100% hexane. Unreacted starting material elutes first followed by the ortho nitro product then by a material hypothesized to be the para nitro compounds. The yield was about 50% of a light yellow solid based on 2,3-dichlorotoluene.

EXAMPLE 2

Preparation of 2,3-dichloro-6-nitrobenzylbromide

In a quartz vessel, 2.4 mmole of 2,3 dichloro-nitrotoluene and 0.2 mmole recrystallized benzoyl peroxide were dissolved in 6 ml anhydrous carbon tetrachloride. 3.0 mmole bromine (dissolved in carbon tetrachloride at 0.5 g/ml) was added and a water condensor and drying tube were attached to the reaction vessel. The mixture was irradiated with a halogen lamp. The reaction tube was loosely covered with foil to retain heat and allow solvent reflux. After the reaction the color had changed from deep red to orange-yellow (about three hours) and starting material was still present. Another equal quantity of bromine (3.0 mmole) was added and the mixture irradiated another three hours. Excess bromine and HBr were then removed under reduced pressure.

The crude product was purified by flash column chromatography using silica gel 60 (35 to 70-um particle size) at 5% product loading. The elution solvent was 25% chloroform in hexane. Impurities and unreacted starting material eluted first followed by the brominated product. The yield was about 70% product (liquid lachrymator) based on 2,3-dichloro-6-nitrotoluene.

EXAMPLE 3

Preparation of ethyl-N-(2,3-dichloro-6-nitrobenzyl) glycine HCl 15 mmole of 2,3-dichloro-6-nitrobenzyl bromide was added to a dry erlenmeyer flask and dissolved with 75 ml anhydrous tetrahydrofuran. 17 mmole glycine, ethyl ester hydrochloride was added and the flask filled with nitrogen. 34 mmole anhydrous triethylamine (dried over (KOH) was added and stirred. A water condensor and drying tube were attached to the flask. The mixture was refluxed for 14 hours and the mixture was filtered and the residue discarded. The solvent was evaporated from the filtrate under reduced pressure. The yield was 99%, crude, based on 2,3-dichloro-6-benzyl bromide.

The crude product was purified by flash column chromatography using silica gel 60 (35 to 70-um particle size) at 3.5% product loading. The elution solvent was 0.5% methanol in chloroform. Impurities and unreacted starting material eluted first, followed by the condensation product.

The yield was 87% pure solid ethyl-N-(2,3-dichloro-6-nitro benzyl) glycine HCl based on the crude product.

The ethyl-N-(2,3-dichloro-6-nitro benzyl) glycine HCl prepared above was used to make Anagrelide by known reactions. Firstly, the ethyl-N-(2,3-dichloro-6-nitro benzyl) glycine HCl is reacted with $SnCl_2$/HCl to form ethyl-N-(2,3-dichloro-6-amino benzyl) glycine HCl. This material is then reacted with CNBr in an inert, aprotic organic solvent such as toluene or chlorobenzene. The formed ethyl-N-(5,6-dichloro-3,4-dihydro-2(1 H) iminoguinazoline-3-acetate HCl is isolated and then reacted with a base such as triethanolamine (TEA) to form Anagrelide. This synthesis process is shown in U.S. Pat. No. 4,146,718, supra. The Anagrelide product produced had the characteristic pharmaceutical properties of commercially available Anagrelide made using for example, the present prior art synthesis process as described above.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A process for the preparation of Compound (C) of the formula:

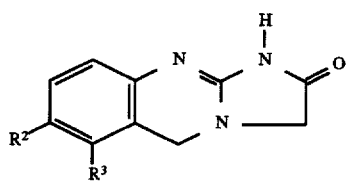

(C)

in which $R^2$ and $R^3$ are the same and are chloro, bromo or iodo; and pharmaceutically acceptable addition salts thereof, which process comprises:

a) nitrating a 2,3 toluene compound of the formula:

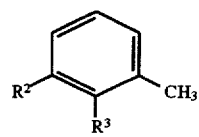

to form compound (F) of the formula:

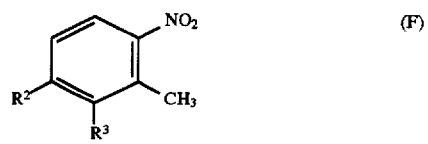

(F)

b) reacting Compound (F) by forming a mixture of compound (F) with a peroxide and chlorine or bromine and irradiating the mixture in a quartz vessel with a halogen lamp to form Compound (G) of the formula:

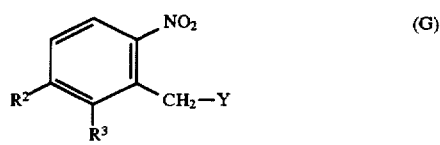

(G)

wherein Y=Cl or Br;

c) reacting Compound (G) with a compound of the formula:

wherein $R^4$ is lower alkyl or H;

to form Compound (E) of the following formula:

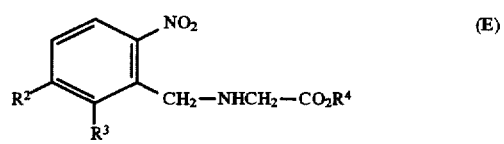

(E)

d) reacting Compound (E) under reducing conditions to form Compound (B):

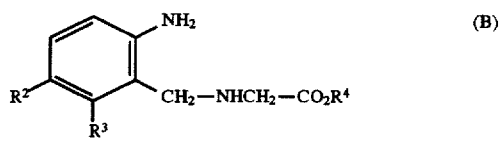

(B)

e) reacting Compound (B) with CNBr, CNCl or CNI to form Compound (D):

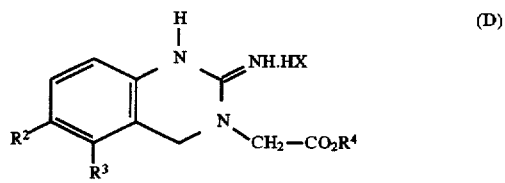

(D)

wherein X is Cl, Br or I; and f) reacting Compound (D) under alkaline conditions to form Compound (C).

2. The process of claim 1 wherein $R^2$ and $R^3$ are both Cl.

3. The process of claim 1 wherein nitration of the compound in step (a) is performed by adding an ambient temperature mixture of concentrated nitric acid and sulfuric acid slowly with stirring to the toluene compound which is maintained in an ice-water bath and then reacting the mixture at an elevated temperature to form compound (F) which is separated from other reaction products and recovered.

4. The process of claim 1 wherein step (c) is performed using anhydrous tetrahydrofuran as a solvent.

* * * * *

UNITED STATES PATENT AND TRADEMARK OFFICE
CERTIFICATE OF CORRECTION

PATENT NO. : 5,801,245
DATED : September 1, 1998
INVENTOR(S) : Phillip C. Lang

It is certified that error appears in the above-identified patent and that said Letters Patent is hereby corrected as shown below:

Column 2, Line 44, " dichloro-nitrobenzonitrile " should be -- dichloro-6-nitrobenzonitrile - -

Column 4, Line 47, "dichloro-nitrotoluene" should be --(dichloro-6-nitrotoluene--.

Column 5, Lines 26,27 and 29,

"nitro benzyl" should be - - nitrobenzyl - -

In the claims:

Claim 1 - Column 6, Line 18:

"compound" should be - - Compound - -

Claim 3 - Column 8, Line 1:

"compound" should be - - Compound - -

UNITED STATES PATENT AND TRADEMARK OFFICE
CERTIFICATE OF CORRECTION

PATENT NO. : 5,801,245
DATED : September 1, 1998
INVENTOR(S) : Phillip C. Lang

It is certified that error appears in the above-identified patent and that said Letters Patent is hereby corrected as shown below:

Column 2, Line 30, replace Compound (E) with the following formula:

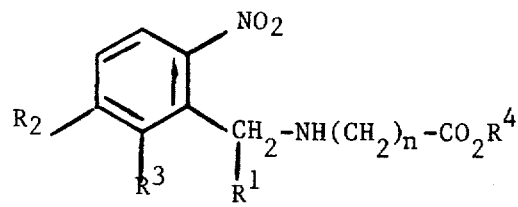

Signed and Sealed this

Second Day of March, 1999

Attest:

Attesting Officer

Q. TODD DICKINSON

Acting Commissioner of Patents and Trademarks